(12) United States Patent
Antoine et al.

(10) Patent No.: US 8,728,743 B2
(45) Date of Patent: May 20, 2014

(54) MICROORGANISMS HAVING INTESTINAL CELL SURFACE GLYCOSYLATION MODULATING ACTION

(75) Inventors: Jean-Michel Antoine, Maisons-Alfort (FR); Miguel Freitas, Paris (FR); Chantal Cayuela, Paris (FR); Germain Trugnan, Montreuil (FR)

(73) Assignee: Compagnie Gervais Danone, Levallois-Perret (FR)

( * ) Notice: Subject to any disclaimer, the term of this patent is extended or adjusted under 35 U.S.C. 154(b) by 1250 days.

(21) Appl. No.: 11/281,738

(22) Filed: Nov. 16, 2005

(65) Prior Publication Data
US 2006/0078548 A1 Apr. 13, 2006

Related U.S. Application Data

(62) Division of application No. 10/332,243, filed on Sep. 11, 2003, now Pat. No. 7,008,785.

(30) Foreign Application Priority Data

Jul. 4, 2000 (FR) ...................................... 00 08672

(51) Int. Cl.
*G01N 33/567* (2006.01)
(52) U.S. Cl.
USPC ............... 435/7.21; 435/4; 435/7.32; 435/29; 435/32
(58) Field of Classification Search
None
See application file for complete search history.

(56) References Cited

U.S. PATENT DOCUMENTS

| | | | |
|---|---|---|---|
| 4,187,321 A * | 2/1980 | Mutai et al. ...................... 426/43 |
| 4,978,745 A * | 12/1990 | Schoemaker et al. ..... 530/387.3 |
| 5,200,314 A * | 4/1993 | Urdea ................................ 435/6 |
| 5,268,486 A * | 12/1993 | Waggoner et al. ............ 548/427 |
| 5,296,221 A | 3/1994 | Mitsuoka et al. |
| 5,338,682 A | 8/1994 | Sasaki et al. |
| 6,541,027 B1 | 4/2003 | Antoine et al. |

FOREIGN PATENT DOCUMENTS

WO  WO 99/29833 A  7/1999

OTHER PUBLICATIONS

Alroy J et al. 1989. Glycoconjugates of the intestinal epithelium of the domestic fowl (*Gallus domesticus*): a lectin histochemistry study. Histochem J 21: 187-193.*
Corfield AP et al. 1992. Mucin degradation in the human colon: production of sialidase, sialate O-acetylesterase, N-acetylneuraminate lyase, arylesterase, and glycosulfatase activities by strains of fecal bacteria. Infect Immun 60: 3971-3978.*
Huet G et al. 1995. Characterization of mucins and proteoglycans synthesized by a mucin-secreting HT-29 cell subpopulation. J Cell Sci 108: 1275-1285.*
Umesaki Y et al. 1995. Segmented filamentous bacteria are indigenous intestinal bacteria that activate intraepithelial lymphocytes and induce MHC class II molecules and fucosyl asialo GM1 glycolipids on the small intestinal epithelial cells in the ex-germ-free mouse.. Microbiol Immunol 39: 555-562.*
XP-001001545 Abstract of Mack DR et al. "Modulation in the expression of intestinal MUC3 mucin by non-pathogenic probiotic microbes", 2000.
Bry Lynn et al., A Model of Host-Microbial Interactions in an Open Mammalian Ecosystem:, Science vo. 273, pp. 1380-1383, Sep. 6, 1996 XP-000993528.
Hooper Lora V. et al., Host-microbial symbiosis in the mammalian intestine; exploring an internal ecosystem: BioEssays 20.4, Apr. 1998, XP-001003006.
Lesuffleur et al., "Growth adaptation to methotrexate of HT-29 human colon carcinoma cells is associated with their ability to differentiate into columnar absorptive and mucus-secreting cell", 1990, Cancer Res., 50:6334-6343.

* cited by examiner

Primary Examiner — Lora E Barnhart Driscoll
(74) Attorney, Agent, or Firm — Patzik, Frank & Samotny Ltd.

(57) ABSTRACT

The invention concerns micro-organism strains, in particular of lactic acid bacteria, having a glycosylation modulating effect of intestinal cell surface. The invention also concerns a method for selecting micro-organism strains, in particular of lactic acid bacteria, which consists in measuring the average fluorescence intensity variation of HT29-MTX cells incubated in the presence of a lectin coupled with a fluorochrome after being in contact with the supernatant of the strain concerned. Said lactic acid bacteria strains can be used, optionally in the form of their active fraction, for preparing food compositions or medicines or food supplements, modulating glycosylation of glycoproteins of intestinal epithelial cells.

8 Claims, No Drawings

MICROORGANISMS HAVING INTESTINAL CELL SURFACE GLYCOSYLATION MODULATING ACTION

CROSS-REFERENCE TO RELATED APPLICATIONS

This is a division of application Ser. No. 10/332,243, filed Sep. 11, 2003 now U.S. Pat. No. 7,008,785.

FIELD OF THE INVENTION

The invention concerns microorganisms having a modulatory effect on surface glycosylation or on the composition of sugars at the surface of intestinal cells, a method for selecting said microorganisms, and their uses in the food and medical sectors.

BACKGROUND OF THE INVENTION

The gastrointestinal mucosa consists of a simple layer of epithelial cells which are at least partially covered on the side of the intestinal lumen by a viscoelastic layer mainly consisting of glycoconjugates. The epithelial cells synthesize the glycoconjugates present at their surface, which are the intermediates in numerous interactions, in particular with lectins or adhesins, with bacterial toxins, or with antibodies, bacteria, viruses, parasites. These glycoconjugates therefore constitute important intermediates in the relationship between the host and the intestinal flora.

These glycoconjugates are, as their name indicates, glycosylated compounds, that is to say on which are grafted sugar chains which are long to a greater or lesser degree and which may be branched. In the healthy human intestine, these sugars may be galactose (Gal), fucose (Fuc), N-acetylneuraminic acid or sialic acid, N-acetylglucosamine (GlcNAc), N-acetylgalactosamine (GalNac), linked to each other by various bonds. Three of them may be in a terminal position; they are galactose, fucose and sialic acid.

A host and its intestinal microflora function as a complex system in which the microflora has a significant impact on the host. In the case of nonpathogenic or probiotic microorganisms, a symbiotic or cooperative relationship often exists between the host and the microorganisms, the presence of the latter being necessary for good balance and good functioning of the host's intestine. By contrast, the presence of pathogenic microorganisms, which is more rare, may have negative consequences by preventing or reducing the presence of probiotic microorganisms, or even by having a parasitic action which is directly harmful to the host.

The fragile balance between the host and the microflora is directly linked to the intestinal environment and in particular to the quantitative and qualitative presence of the surface glycoconjugates. Indeed, it is known that some microorganisms, which may be probiotic or pathogenic, will be sensitive to certain sugars at the terminal position. The intestinal bacteria can modulate the pattern of glycosylation of the glycoconjugates present at the surface of the intestinal cells, without their mode of action being completely elucidated as will be seen hereinafter. The bacteria can, on the one hand, induce the presence of such and such sugar during glycosylation and, on the other hand, break down the sugars present at the terminal position of a chain, which qualitatively and/or quantitatively modifies the sugars present at the terminal position.

This modulation of the pattern of epithelial cell surface glycosylation causes modification of the intestinal environment, it being possible for the modified environment to promote the establishment of certain microorganisms and/or to limit, or even avoid, the establishment of other microorganisms. Modification of the environment, which may be generated by the microflora, therefore has a direct impact on the balance between the host and the microflora.

It would therefore be highly advantageous to have a model which makes it possible to rapidly and easily select microorganisms according to their action on the pattern of glycosylation. It would thus be possible to identify microorganisms promoting the presence of one sugar or another, and therefore promoting the establishment of beneficial microorganisms such as, for example, probiotics and/or limiting the establishment of pathogenic microorganisms.

Indeed, to the knowledge of the applicant, no microorganisms, in particular lactic acid bacteria, have so far been identified which are capable of finely acting accurately on the glycosylation pattern, and thus of accurately modulating this glycosylation pattern and therefore the implantation of microorganisms.

Such microorganisms modulating the glycosylation pattern could find a use in particular in pharmaceutical or food compositions or food supplements. Indeed, they can make it possible to optimize the functioning of the intestinal cells and the good balance of the microflora.

The document WO 99/29833 describes a novel bacterial strain having certain properties, for example an antimicrobial activity. However, the modalities of its action are not detailed, and in particular the question of the possible action of the bacterium on sugars is never addressed.

Bry L. et al., in "A model of host-microbial interactions in an open mammalian ecosystem", Science, Vol. 273, pp. 1380-1383, Sep. 6, 1996, studied in vivo (in mice) the influence of *Bacteroides thetaiotaomicron* on fucosylation. *Bacteroides thetaiotaomicron* is part of the intestinal flora in humans and in mice. The model used is nevertheless limited to the study of fucosylation, with the exclusion of other types of glycosylation. It is moreover an in vivo model, and therefore longer and more complex to use than an in vitro model.

However, this model made it possible to emit the hypothesis of the existence of a soluble factor secreted by *B. thetaiotaomicron*, and which is thought to play the role of a signal bringing about the modification of surface glycosylation. This unidentified soluble factor is therefore thought to act without there being direct contact between the bacteria and the target cells.

To the knowledge of the applicant company, no method has been developed to date which makes it possible to select in vitro, easily and rapidly, various microorganisms, in particular various strains of lactic acid bacteria, according to their precise action on the pattern of glycosylation of the intestinal epithelial cells, and more precisely on the modulation or variation of the composition of each of the sugars.

In the context of the present application, the term "lactic acid bacteria" denotes bacteria capable of producing lactic acid, and in particular the nonpathogenic bacteria chosen from the group comprising *Streptococcus, Lactobacillus, Lactococcus, Bifidobacterium* and *Leuconostoc*, in particular *B. breve, B. longum, L. lactis, S. thermophilus, L. casei, L. helveticus* and *L. bulgaricus*.

OBJECTS AND DESCRIPTION OF THE INVENTION

A subject of the present invention is therefore such a method of selection in vitro, which comprises the following steps:

bringing the culture supernatant for the strain of microorganisms, in particular of lactic acid bacteria, into contact with cells of a cell line model representing the intestinal epithelial cells,
incubating,
extracting the cells and incubating with various lectins coupled to a fluorochrome,
washing,
measuring the mean fluorescence intensity (MFI) of each lectin, comparing with the measurements performed on a control sample in order to evaluate the variation in MFI induced by the bacteria, selecting the strain of microorganisms inducing a variation of at least 20% for at least one sugar.

The latter step may in particular be carried out on plates, the measurement of MFI being performed by a probe, according to techniques known to persons skilled in the art, or by flow cytometry. In the case of flow cytometry, it is also possible to compare the graph obtained, representing the variation of fluorescence as a function of the number of cells, with that obtained with a control sample, and to select the strain of microorganisms inducing a variation in the shape of the graph.

Any cell line model representing intestinal epithelial cells may be used in this method of selection. Persons skilled in the art will know how to choose an appropriate cell line model among the known models, for example the lines Caco-2 or HT29-MTX, which are cancerous intestinal epithelial cells in culture. These lines are considered as reproducing all or some of the mechanisms of regulation of the systems in vivo and in particular the production of glycoconjugates. Any line exhibiting this characteristic may be used in the method according to the invention. As regards the HT29-MTX line, reference may be made to Lesuffleur et al., "Growth adaptation to methotrexate of HT-29 human colon carcinoma cells is associated with their ability to differentiate into columnar absorptive and mucus-secreting cells", 1990, Cancer Res., 50:6334-6343.

Centrifugation and filtration of the culture medium in which each strain of microorganisms to be tested has been incubated are carried out in order to extract the ("trial") supernatant therefrom. Without wishing to be bound by any theory, the applicant considers that the supernatant contains the soluble factor constituting the signal for modulating glycosylation. The supernatant therefore constitutes an active fraction of a strain of microorganisms. Brought into contact with the intestinal epithelial cells, it will cause or not one or another modification of glycosylation according to the strain of microorganisms tested.

Thus, in *Bacteroides*, the soluble factor was identified as being a low molecular weight molecule (less than 8 kD) and that it is heat-sensitive. It can be assumed that the soluble factor from another strain will exhibit similar, if not identical, characteristics.

The supernatant obtained from the culture medium which has not been in contact with the bacteria is used as a "control".

An appropriate quantity of the "trial" and "control" supernatants are incorporated into the culture medium in which the cells of the cell line model, for example HT29-MTX, are placed for an appropriate period. This period may be, for example, from 1 to 15 days.

In a particular embodiment, it is possible to add bacteria in place of the supernatant. In this case, the bacteria may be added in the form of a suspension in the presence of penicillin G and of a strong buffer making it possible to inhibit bacterial development without preventing the viability of the bacteria, and acidification of the medium.

After this period of incubation, the cells of the cell line model are detached and resuspended, and the same number of "trial" and "control" cells is incubated separately with a lectin of which the specificity toward sugars (nature of the sugar, nature of the linkage) is known.

Each lectin, which is coupled to a fluorochrome, will bind to the sugar for which it is specific.

The "trial" and "control" cell suspensions are each washed several times, and the reactivity of each lectin is quantified by fluorescence measurements called MFI (mean fluorescence intensity).

This measurement may be carried out by any appropriate means, in particular by means of flow cytometry (FACScan, Bencton-Dickinson) or by direct fluorimetric measurements on plates.

When flow cytometry is used, a graph representing the variation of fluorescence as function of the number of cells is obtained for each lectin. For each flow cytometry graph, the mean fluorescence intensity corresponds to the median value.

Two comparisons are possible. On the one hand, regardless of the mean of the measurement of fluorescence intensity, it is possible to compare quantitatively the "trial" MFI with the "control" MFI. On the one hand, in the case of flow cytometry, it is also possible to compare qualitatively the "trial" result with the "control" result, and more precisely to compare the graph obtained with the "trial" suspension with that obtained with the "control" suspension, that is to say to compare the shape of the curves.

It is estimated that a decrease or an increase in this MFI of at least about 20%, preferably at least about 28%, still more preferably at least about 35%, reveals a significant change in the reactivity of each lectin, and therefore of the sugar composition of the glycoproteins present at the surface of the epithelial cells.

This method therefore makes it possible to observe and to quantify in a simple and rapid manner the presence of each lectin on the sugar chains, and therefore to quantify the sugar whose lectin is specific. It is then possible to compare the values obtained without and with microorganisms, and thus to evaluate the glycosylation modulating effects of each strain of microorganisms, in order to select the strains having the desired effect: increase in such a sugar, decrease in another.

The subject of the invention is also the strains of microorganisms, in particular of lactic acid bacteria, capable of modulating the pattern of intestinal epithelial cell surface glycosylation, and more particularly the strains of microorganisms, in particular of lactic acid bacteria, capable of being selected by the method described above.

Such microorganisms therefore make it possible to modulate glycosylation, and therefore to reestablish or modify the intestinal environment in order to promote the establishment of probiotic microorganisms and to avoid or limit the establishment of pathogenic microorganisms.

It is known, for example, that the receptor allowing adhesion of *Escherichia coli* contains galactose and sialic acid; for *Streptococcus pyogenes* and *Listeria monocytogenes*, it is galactose; for *Helicobacter pylori*, it is fucose; and for *Entamoeba histolytica*, it is galactose and N-acetylgalactosamine.

The strains which are the subject of the invention may be in particular the following strains: CNCM collection No. I-2492, CNCM collection No. I-2493, CNCM collection No. I-2494 (CNCM=Collection Nationale de Cultures de Microorganismes—Institut Pasteur—28, rue du Dr. Roux—75724 Paris Cedex 15—France), deposited on 20 Jun. 2000.

It is possible to use such microorganisms, in particular such lactic acid bacteria, or their active fraction, that is to say the fraction comprising the soluble factor, for the preparation of food compositions or medicaments or food supplements modulating intestinal epithelial cell surface glycosylation. These compositions may comprise a single strain, or several strains, of microorganisms modulating glycosylation.

Thus, compositions are available which make it possible to maintain or reestablish a proper host-intestinal flora balance, or which make it possible to promote the establishment of one or another strain of microorganisms. They therefore make it possible to optimize the functioning of the intestinal cells and good balance of the microflora. It is possible in particular to use lactic acid bacteria, and to incorporate them into dairy products.

The strains tested in the trials below are given by way of nonlimiting examples.

Lactic Acid Bacteria in Vitro Trials

Centrifugation and filtration of the culture medium in which lactic acid bacteria (LAB) have been incubated overnight were carried out in order to extract the ("trial") supernatant therefrom.

The LAB strains used are the following: CNCM collection No. I-2492, CNCM collection No. I-2493, CNCM collection No. I-2494.

The supernatant obtained from the culture medium which has not been in contact with the bacteria is used as a "control".

An optimum quantity for each "trial" and "control" supernatant (between 10% and 30%) is incorporated into the DMEM ("Dulbecco's Modified Eagle's Medium") culture medium in which the HT29-MTX cell line is placed for 5 to 15 days.

After this treatment, the HT29-MTX cells are detached and resuspended in a PBS solution ("Phosphate Buffered Saline Solution"), and the same number of "trial" and "control" cells is incubated separately with a lectin specific for a sugar (nature of the sugar, nature of the linkage) at optimum concentration for 30 minutes.

The commercial lectins used and their epitope(s) are the following:

| Lectin Name | Lectin Abbreviation | Epitope(s) |
|---|---|---|
| Artocarpus integrifolia | Jak | Gal |
| Ricinus communis | RCA I | Gal |
| Griffonia simplicifolia I B4 | GSI-B4 | Galα3Gal |
| Helix pomatia | HPA | GalNAc |
| Datura stramonium | DSA | GlcNAc |
| Wheat germ | WGA | GlcNAc and sialic acid |
| Anguilla anguilla | AAA | α-L-fucose |
| Ulex europaeus I | UEA I | Fucα2Galβ |
| Maackia amurensis | MAA | sialic ac. α 2, 3 |
| Sambucus nigra | SNA | sialic ac. α 2, 6 |

All these lectins are marketed by EY Laboratories Inc. (San Mateo, Calif., USA) except RCA I, marketed by Sigma Aldrich (Saint-Quentin-Fallavier, France).

The following mean fluorescence intensity values are obtained by flow cytometry for each strain of lactic acid bacteria, and for the "control" and "trial" cells:

| Lectin | "control" | "trial" | Variation |
|---|---|---|---|
| CNCM I-2492 | | | |
| RCA | 424 | 392 | −7.5% |
| Jak | 422 | 431 | +2% |
| DSA | 237 | 241 | +1.6% |
| SNA | 57 | 48 | −16% |
| HPA | 334 | 350 | +4.5% |
| CNCM I-2493 | | | |
| Jak | 535 | 392 | −26.7% |
| SNA | 48 | 36 | −25% |
| HPA | 354 | 379 | +7% |
| MAA | 665 | 518 | −22% |
| WGA | 1313 | 1376 | +4.8% |
| GSI | 37 | 31 | −16% |
| RCA | 317 | 247 | −22% |
| DSA | 176 | 165 | −6% |
| CNCM I-2494 | | | |
| Jak | 346 | 446 | +29% |
| SNA | 34 | 35 | +2.9% |
| HPA | 748 | 593 | −20.7% |
| AAA | 10 | 20 | +100% |
| MAA | 668 | 644 | −3.6% |
| WGA | 302 | 290 | −4% |
| GSI | 30 | 32 | +6.7% |
| RCA | 258 | 369 | +43% |
| DSA | 176 | 198 | +11% |

Thus, the glycosylation modulating action of each bacterial strain can be immediately observed. For example, it can be observed that the CNCM I-2494 strain causes an increase in Gal and α-L-Fucose, and a decrease in GalNAc.

The invention claimed is:

1. A method of selecting strains of microorganisms for use in a food product that induce a modulation of the pattern of surface glycosylation or of sugar composition of intestinal epithelial cells, said method comprising the following steps:
  (a) providing a supernatant from a culture of a strain of microorganism to be tested ("trial supernatant"), and a culture medium which has not been in contact with bacteria ("control supernatant"),
  (b) providing cells of a cell line model reproducing all or some of the mechanisms of glycolysate production in intestinal epithelial cells,
  (c) providing a lectin coupled to a fluorochrome, wherein said lectin is specific towards a sugar,
  (d) bringing into contact and incubating the trial supernatant from step (a) with cells from step (b) recovering the resulting cells, incubating the recovered cells with said lectin from step (c) washing the resulting cells, and then measuring the resulting mean fluorescence intensity (MFI) of the fluorochrome coupled to said lectin,
  (e) bringing into contact and incubating the control supernatant from step (a) with cells from step (b), recovering the resulting cells, incubating the recovered cells with said lectin from step (c), washing the resulting cells, and then measuring the resulting mean fluorescence intensity (MFI) of the fluorochrome coupled to said lectin,
  (f) comparing the MFI of step (d) with the MFI of step (e), wherein a difference of at least 20% indicates that said strain of microorganism induces a modulation of the pattern of surface glycosylation or of sugar composition of intestinal epithelial cells; and
  (g) introducing into said food product said strain of microorganism selected from step (f) which exhibit an MFI differential of at least 20%.

2. The method as claimed in claim 1, wherein the mean fluorescence intensity is measured by flow cytometry.

3. The method as claimed in claim 1, wherein the microorganisms are bacteria.

4. The method as claimed in claim 3, wherein the bacteria are lactic acid bacteria.

5. The method as claimed in claim 1, wherein the strain of microorganisms selected induces a variation in MFI of at least about 28%.

6. The method as claimed in claim 5, wherein the strain of microorganisms selected induces a variation in MFI of at least about 35%.

7. The method as claimed in claim 1, wherein the cells provided at step (b) are HT29-MTX cells.

8. A method of selecting strains of Bifidobacteria for use in a food product that induce a modulation of the pattern of surface glycosylation or of sugar composition of intestinal epithelial cells, said method comprising the following steps:
(a) providing a supernatant from a culture of a strain of Bifidobacteria to be tested ("trial supernatant"), and a culture medium which has not been in contact with bacteria ("control supernatant"),
(b) providing cells of a cell line model reproducing all or some of the mechanisms of glycolysate production in intestinal epithelial cells,
(c) providing a lectin coupled to a fluorochrome, wherein said lectin is specific towards a sugar,
(d) bringing into contact and incubating the trial supernatant from step (a) with cells from step (b) recovering the resulting cells, incubating the recovered cells with said lectin from step (c) washing the resulting cells, and then measuring the resulting mean fluorescence intensity (MFI) of the fluorochrome coupled to said lectin,
(e) bringing into contact and incubating the control supernatant from step (a) with cells from step (b), recovering the resulting cells, incubating the recovered cells with said lectin from step (c), washing the resulting cells, and then measuring the resulting mean fluorescence intensity (MFI) of the fluorochrome coupled to said lectin,
(f) comparing the MFI of step (d) with the MFI of step (e), wherein a difference of at least 20% indicates that said strain of Bifidobacteria induces a modulation of the pattern of surface glycosylation or of sugar composition of intestinal epithelial cells; and
(g) introducing into said food product said strain of Bifidobacteria selected from step (f) which exhibit an MFI differential of at least 20%.

* * * * *

UNITED STATES PATENT AND TRADEMARK OFFICE
CERTIFICATE OF CORRECTION

PATENT NO. : 8,728,743 B2
APPLICATION NO. : 11/281738
DATED : May 20, 2014
INVENTOR(S) : Jean-Michel Antoine et al.

Page 1 of 1

It is certified that error appears in the above-identified patent and that said Letters Patent is hereby corrected as shown below:

On the title page, left column, under "Related U.S. Application Data", item (62) should read as follows:

--Division of application No. 10/332,243, filed on Sep. 11, 2003, now Pat. No. 7,008,785, which is a 371 of PCT/FR01/02147, filed July 4, 2001--

Signed and Sealed this
Twenty-first Day of July, 2015

Michelle K. Lee
*Director of the United States Patent and Trademark Office*